United States Patent [19]
Ponsy

[11] Patent Number: 5,328,664
[45] Date of Patent: Jul. 12, 1994

[54] PREPACKAGED FLUID TEST SYSTEM FOR DETERMINING LEVELS OF A SUBSTANCE

[76] Inventor: Jacques Ponsy, Ancien Chemin de Saint Privat, 34150 Arboras, France

[21] Appl. No.: 950,874

[22] Filed: Sep. 24, 1992

[30] Foreign Application Priority Data

Sep. 24, 1991 [FR] France ................. 91 12272

[51] Int. Cl.$^5$ .................. G01N 31/22; G01N 21/29
[52] U.S. Cl. .................................. 422/84; 422/83;
422/85; 422/86; 422/58; 422/102; 422/104;
436/132; 206/222; 222/81; 222/83; 222/83.5
[58] Field of Search ................. 222/81, 83, 83.5;
206/219, 222; 422/83, 84–86, 58, 59, 60, 102,
104; 436/132

[56] References Cited

U.S. PATENT DOCUMENTS

| | | | |
|---|---|---|---|
| 1,977,580 | 10/1934 | Grier | 206/219 X |
| 2,371,405 | 3/1945 | Munn | 422/59 |
| 2,487,077 | 11/1949 | Shepherd | 422/59 |
| 2,569,895 | 10/1951 | Main-Smith et al. | 422/86 |
| 3,223,488 | 12/1965 | Luckey | 422/85 |
| 3,613,955 | 10/1971 | Wetherell | 206/222 X |
| 3,676,073 | 7/1972 | Luckey | 422/84 X |
| 4,022,578 | 5/1977 | Kretschmer | 422/60 X |
| 4,201,208 | 5/1980 | Cambio, Jr. | 222/83 X |
| 4,329,318 | 5/1982 | Le Grouyellec et al. | 422/85 X |
| 4,353,869 | 10/1982 | Guth | 422/85 X |
| 4,769,218 | 9/1988 | Leichnitz et al. | 422/86 |
| 4,894,269 | 1/1990 | Kimura | 206/222 X |
| 4,962,852 | 10/1990 | Affaitati et al. | 206/222 |
| 4,971,762 | 11/1990 | Bäther | 422/86 X |
| 5,171,535 | 12/1992 | Lamont | 422/84 X |

FOREIGN PATENT DOCUMENTS 2497954 7/1982 France .
WO85/04016 9/1985 PCT Int'l Appl. .

Primary Examiner—James C. Housel
Assistant Examiner—Milton I. Cano
Attorney, Agent, or Firm—Herbert Dubno; Andrew Wilford

[57] ABSTRACT

A device for determining the levels of a predetermined substance in a predetermined volume of a fluid has an inner tube, a mass in the inner tube of a material that changes properties when exposed to the substance so that when the fluid passes through the mass the substance changes, an outer protective tube surrounding the inner tube and having an open end, a frangible seal sheet covering the open outer-tube end, and a test element having an end pierceable through the sheet and fittable with an end of the inner tube. Thus to install the cartridge formed by the inner tube and its contents on the test element, same is merely poked through the seal to simultaneously open the package and fit over the inner tube.

7 Claims, 1 Drawing Sheet

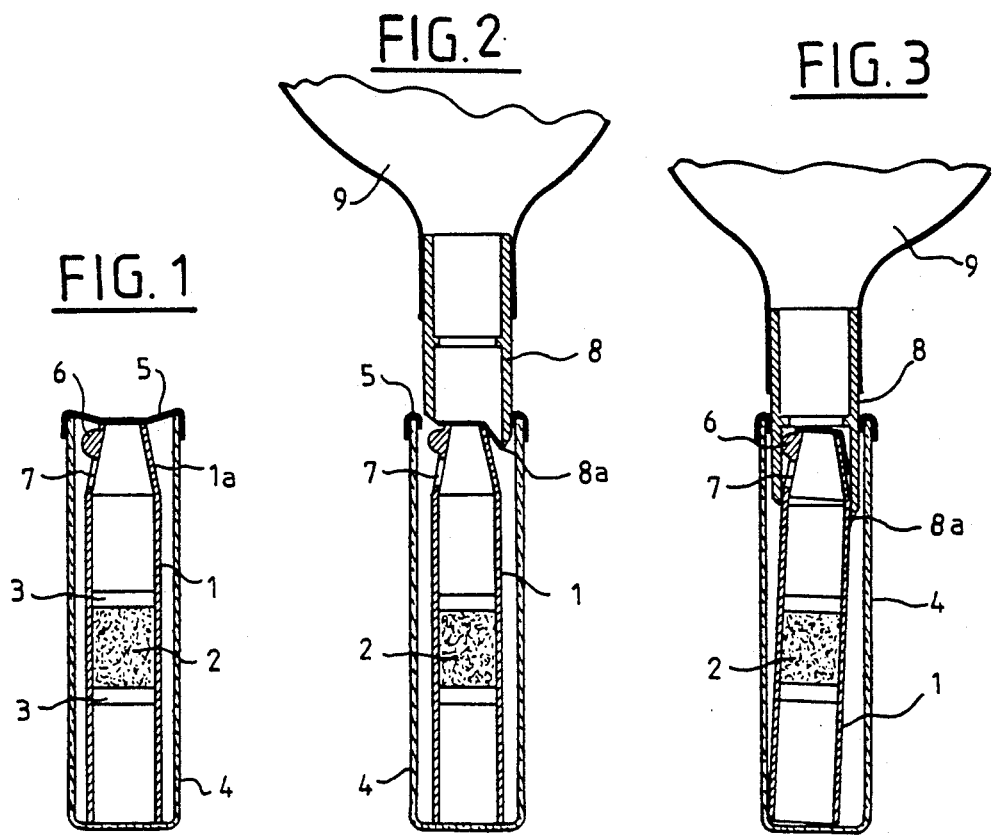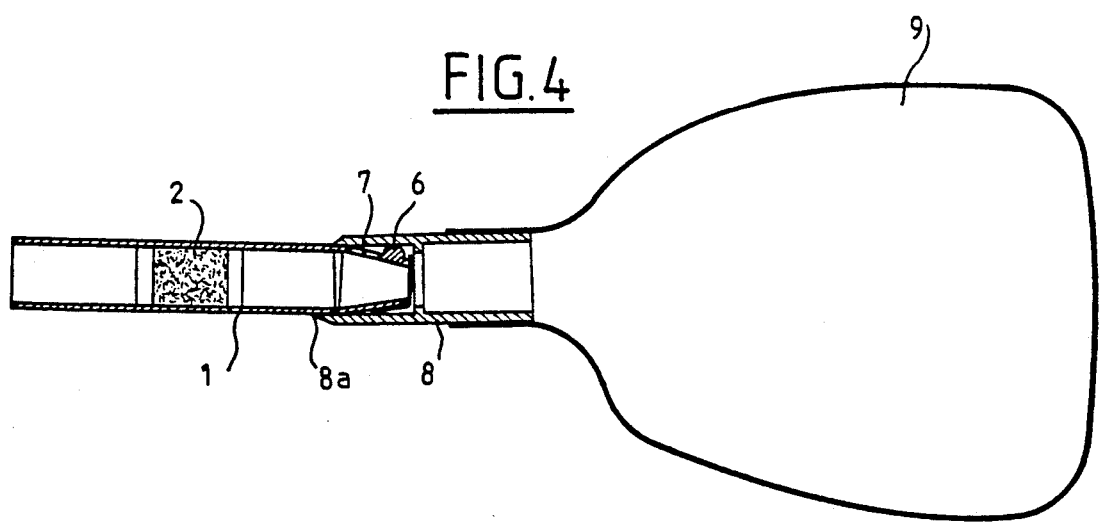

PREPACKAGED FLUID TEST SYSTEM FOR DETERMINING LEVELS OF A SUBSTANCE

FIELD OF THE INVENTION

The present invention relates to a prepackaged fluid test system. More particularly this invention concerns a test cartridge for a gas-test device.

BACKGROUND OF THE INVENTION

A gas-test device of the type used, for example, as a so-called breathalyzer to test the alcohol content of the exhalations of a drunk-driving suspect normally comprises a glass tube defining a fluid-flow passage in which is provided a mass of particles that, when they react to the alcohol component of a stream of gas passing through them, change color. In the standard drunkometer test the suspect is required to inflate a balloon, thereby passing a measured volume of his or her exhalations through the test cartridge to determine the alcohol level in the volume of gas held by the balloon.

A problem with such devices is that the cartridge containing the reactive material must be kept in a sealed environment and only at the last minute is fitted to the mouthpiece of the balloon to run the test. Any minor difficulties make the test invalid so that handling of the delicate cartridge must be minimized.

Another problem with the known devices is that the crystals that hold the reactive substance get powdered by rough handling so that they no longer work properly.

OBJECTS OF THE INVENTION

It is therefore an object of the present invention to provide an improved fluid test system.

Another object is the provision of such an improved fluid test system which overcomes the above-given disadvantages, that is which is easy to use.

A further object is to provide such an improved test system where the reactive material is particularly well protected.

SUMMARY OF THE INVENTION

A device for determining the levels of a predetermined substance in a predetermined volume of a fluid has according to the invention an inner tube, a mass in the inner tube of a material that changes properties when exposed to the substance so that when the fluid passes through the mass, the material changes, an outer protective tube surrounding the inner tube and having an open end, a frangible seal sheet covering the open outer-tube end, and a test element having an end pierceable through the sheet and fittable with an end of the inner tube. Thus to install the cartridge formed by the inner tube and its contents on the test element, same is merely poked through the seal to simultaneously open the package and fit over the inner tube. The person running the test in fact does not have to touch the inner tube at all, eliminating any possibility that the test results could be questioned because of such mishandling.

According to the invention the inner-tube end is tapered, is formed with a laterally throughgoing hole, and is formed adjacent the hole with a laterally projecting bump. Furthermore the end of the test element is tubular and sharpened and has an inside diameter generally equal to an outside diameter of the inner tube. The inner tube forms a passage opening laterally at the hole and the frangible seal is engaged over and sealed to the inner tube.

BRIEF DESCRIPTION OF THE DRAWING

The above and other objects, features, and advantages will become more readily apparent from the following, reference being made to the accompanying drawing in which:

FIG. 1 is an axial section through a packaged test cartridge according to the invention;

FIGS. 2 and 3 are views like FIG. 1 showing how the test cartridge is mounted on a test device; and FIG. 4 is another axial section showing the cartridge in the use position.

SPECIFIC DESCRIPTION

As seen in FIG. 1 a glass tube 1 contains a mass 2 of chemical-containing silica-gel particles held in place between two perforated membranes or partitions 3 and doped with a reactive substance. The tube 1 is basically cylindrical, with one end 1a tapered frustoconically and formed with a lateral radially throughgoing hole 7 and immediately adjacent the hole 7 with a bump or boss 6. The elements 1-3 form a test cartridge here intended for use as a breath analyzer for a drunk-driving test kit.

The tube 1 is held in a glass tube-envelope 4 of basically cylindrical shape with a closed bottom. Its top is closed by a heat-sealed membrane or sheet 5 that is also sealed to the upper end of the tube 1. Thus this sheet 5 not only contains the tube 1 and its contents 2 in a dry pure atmosphere inside the outer tube 4, but it also physically stabilizes the tube 1 inside the tube 2 so that it cannot rattle therein, thereby powdering the particle mass 2 and rendering it useless. The tubes 1 and 4 are roughly of the same length.

To use the system a mouthpiece tube 8 carrying a balloon 9 is pushed through the seal 5. This tube 8 has an outer diameter that is slightly less than the inner diameter of the tube 4 and an inner diameter that is virtually the same as the outer diameter of the tube 1. In addition this tube 8 has an angled and sharp-edged end 8a that is intended specifically to poke and cut through the foil or sheet 5.

Thus when the mouthpiece 8 is thrust through the membrane 5 into the outer tube 4 it will simultaneously cut through the seal 5 and fit over the upper end of the tube 1. The bump 6 ensures that the mouthpiece 8 will not lie directly on and block the opening 7. Once thus fitted together the mouthpiece 8 can be pulled back out of the outer tube 4, taking with it the inner tube 1 which is snugly force-fitted into its end 8a.

The balloon 9, is then inflated with the suspect's exhalations, to force these gases back through the reactive mass 2, thereby creating the desired dosed reaction. Once the test is complete the unit 1-3 is normally discarded, unless of course it is held as evidence.

I claim:

1. A device for determining the level of a predetermined substance in a predetermined volume of a fluid, the device comprising:
    an inner tube having a pair of ends;
    a mass in the inner tube of a material that changes properties when exposed to the substance in the fluid, whereby when the fluid passes through the mass the material changes by producing a color change;

an outer protective tube surrounding the inner tube and having an open end juxtaposed with one of the ends of the inner tube;

a frangible seal sheet covering the open outer-tube end;

a test element having a pair of ends one of which has means for piercing through the frangible sheet and means for frictionally fitting an inner diameter of the test element with an outer diameter of the inner tube; and a balloon mounted on the other end of the test element, whereby upon engagement of the fitting means of the test member with the inner tube, the piercing means simultaneously cuts the fringible seal sheet allowing the inner tube to be pulled back out from the outer tube.

2. The device defined in claim 1 wherein the frangible seal is engaged over and sealed to the end of the inner tube.

3. A device for determining the level of a predetermined substance in a predetermined volume of a fluid, the device comprising:

an inner tube having a tapered end formed with a laterally throughgoing hole, and formed immediately adjacent the hole with a laterally and outwardly projecting bump;

a mass in the inner tube of a material that changes properties when exposed to the substance in the fluid, whereby when the fluid passes through the mass the material changes by producing a color change;

an outer protective tube surrounding the inner tube and having an open end juxtaposed with the inner-tube tapered end;

a frangible seal sheet covering the open outer-tube end;

a test element having a pair of ends one of which has means for piercing through the frangible sheet and means for frictionally fitting an inner diameter of the test element with an outer diameter of the inner tube, the bump being so positioned adjacent relative to the hole and the test-element end being so dimensioned that when the test-element end is engaged over the inner-tube tapered end the bump holds the test element away from the throughgoing hole, whereby upon engagement of the fitting means of the test member with the inner tube, the piercing means simultaneously cuts the fringible seal sheet allowing the inner tube to be pulled back out from the outer tube.

4. The device defined in claim 3 wherein the piercing means is tubular and sharpened and has an inside diameter generally equal to an outside diameter of the inner tube and an outside diameter smaller than an inside diameter of the outer tube.

5. The device defined in claim 3 wherein the inner tube forms a passage opening laterally at the hole.

6. A test assembly for determining the level of a substance in a gas, the assembly comprising:

a cartridge having an inner tube having a length and a pair of open ends, and a mass of a reactive material in the tube between its ends capable of changing properties when exposed to the substance, whereby when the gas is passed through the mass the material changes by producing a color change;

an outer package tube having one closed end and an opposite open end and of a length between its ends generally equal to the length of the inner tube, the inner tube being in the outer tube and having one of its open ends generally level with the open end of the outer tube;

a seal foil engaged over the open end of the outer tube and also adhered to the respective open end of the inner tube, whereby the seal foil closes the outer tube and stabilizes the inner tube in the outer tube;

a test element having a pair of ends one of which has means for piercing through the seal foil and means for frictionally fitting an inner diameter of the test element with an outer diameter of the inner tube; and a balloon fitted over the other end of the test element, whereby upon engagement of the fitting means of the test member with the inner tube, the piercing means simultaneously cuts the seal foil allowing the inner tube to be pulled back out from the outer tube.

7. The test assembly defined in claim 6 wherein the end of the inner tube at the open end of the outer tube is outwardly tapered, the piercing means having a sharpened end being of an outside diameter smaller than an inside diameter of the open end of the outer tube and an inside diameter generally equal to an outside diameter of the inner tube.

* * * * *